United States Patent
Schmaus et al.

(10) Patent No.: US 6,863,779 B2
(45) Date of Patent: Mar. 8, 2005

(54) DISTILLATION OF STYRENE

(75) Inventors: Paulus Schmaus, Ludwigshafen (DE); Werner Georg Metzger, Hessheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/922,162

(22) Filed: Aug. 6, 2001

(65) Prior Publication Data

US 2002/0040845 A1 Apr. 11, 2002

(30) Foreign Application Priority Data

Aug. 5, 2000 (DE) .......................................... 100 38 349

(51) Int. Cl.$^7$ .............................. B01D 3/34; C07C 7/05; C07C 7/20
(52) U.S. Cl. ............................... 203/8; 203/49; 203/64; 203/91; 585/804; 585/864
(58) Field of Search ............................ 203/1–3, 63–64, 203/49, 91, 98, 100, 8–9; 585/3, 6, 804, 864, 4, 5

(56) References Cited

U.S. PATENT DOCUMENTS

| 4,466,904 A | | 8/1984 | Watson et al. ............... 252/402 |
| 4,468,343 A | | 8/1984 | Butler et al. ................ 252/403 |
| 4,487,981 A | * | 12/1984 | Miller et al. .................. 544/35 |
| 4,835,326 A | * | 5/1989 | Daren et al. ................ 570/105 |

FOREIGN PATENT DOCUMENTS

| DE | 2006863 | * | 2/1970 |
| EP | 04 403 672 | | 12/1990 |
| JP | 50002498 | * | 1/1975 |

OTHER PUBLICATIONS

Kemmere et al, "The influence of 4–tert–butylcatechol on the emulsion polymerization of Styrene" Journal of Applied Polymer Science, 71(14), 1999' 130:237918.*

* cited by examiner

Primary Examiner—Virginia Manoharan
(74) Attorney, Agent, or Firm—Keil & Weinkauf

(57) ABSTRACT

A process for the distillation of vinylaromatic monomers in the presence of 4-tert-butylcatechol (TBC) and oxygen, wherein no aromatic nitro or amino compound is present in any effective amount. The process is particularly suitable for destabilizing and purifying styrene which has been stabilized with 4-tert-butylcatechol (TBC) for transportation.

7 Claims, No Drawings

DISTILLATION OF STYRENE

The invention relates to a process for the distillation of vinylaromatic monomers in the presence of 4-tert-butylcatechol and oxygen.

In order to increase its stability in storage, styrene is usually shortstopped with from 10 to 20 ppm of 4-tert-butylcatechol (TBC) and stored in the presence of traces of oxygen.

Sulfur, nitrophenols and nitroxyl compounds, for example, are known to be useful for prevention of polymerization during distillation.

WO 96/16921 describes prolongation of the inhibition period during the distillation of styrene in the presence of nitroxyl inhibitors and small amounts of oxygen.

Synergistic inhibitor mixtures of 2,6-dinitro-p-cresol and phenylenediamine or 4-tert-butylcatechol are described in U.S. Pat. No. 4,468,343 and like mixtures of phenothiazines, 4-tert-butylcatechol and 2,6-dinitro-p-cresol are described in U.S. Pat. No. 4,466,904. These polymerization inhibiting systems are used in the presence of oxygen.

The inhibitor systems described for the distillation of styrene possess a comparatively high degree of toxicity or are relatively expensive.

It is thus at object of the invention to find a cheap process for the distillation of styrene. Another object is to find an advantageous and efficient process for the destabilization and purification of styrene to which 4-tert-butylchatechol has been added for transportation.

Accordingly we have found a process for the distillation of vinylaromatic monomers in the presence of 4-tert-butylcatechol (TBC) and oxygen, wherein no aromatic nitro or amine compound is present in any effective amount.

The vinylaromatic monomer used can be, for example, styrene, α-methylstyrene, vinyl toluene, divinyl benzene, styrenesulfonic acid or a mixture thereof. The process is preferably used for the distillation of styrene.

Distillation can be carried out in conventional distillation assemblies, such as multi-plate, packed or unpacked distillation columns. For the purpose of destabilizing and purifying styrene to which 4-tert-butylchatechol has been added for transportation, it is usually sufficient to use a distillation column having one plate or a simple evaporator.

In a preferred embodiment, the 4-tert-butylcatechol (TBC) is fed to the distillation apparatus together with the vinylaromatic monomer. Preferably the concentration of 4-tert-butylcatechol at the bottom of the column is in the range of from 100 to 15,000 ppm, particularly from 5,000 to 10,000 ppm, based on the vinylaromatic monomer.

In addition to 4-tert-butylcatechol there can be added polymerization inhibitors such as are conventionally employed for the distillation of styrene. Examples thereof are nitroxyl inhibitors, particularly sterically hindered nitroxyl compounds such as are described in WO 96/16921. However, the process of the invention is distinguished by the fact that the addition of further polymerization inhibitors is not usually necessary.

The process of the invention is usually carried out at temperatures ranging from 40° to 125° C. and preferably from 60° to 80° C.

Since any oxygen dissolved in the styrene is rapidly consumed under the said distillation conditions, oxygen should be additionally fed to the distillation apparatus, for example by metering an oxygen-containing gas to the bottom of the distillation column through a gas spray.

Better distribution of oxygen in the vinylaromatic monomers is achieved however, when pure oxygen or an oxygen-containing gas, for example air, is mixed in with the stream being fed to the distillation assembly. Preferably an oxygen-containing gas is metered in by a circulating pump mounted on the suction side upstream of the distillation apparatus. This dosage method has the additional advantage that polymerization is inhibited before the vinylaromatic monomer can come into contact with the hot surfaces of the heat exchanger. The oxygen can be metered in at various points, if desired.

The amount of oxygen fed in is governed by the polymerizability of the monomers used and the distillation conditions. The amount may never be so high that an explosive monomer/oxygen mixture is formed. Advantageously the oxygen is metered in at a rate of from 0.01 to 0.5 wt % and preferably from 0.05 to 0.1 wt %, based on the weight of vinylaromatic monomer.

We have found that the polymer content of the bottoms can be significantly reduced by this measure. Following the addition of oxygen, said content is usually below 1.2%, which is equivalent to a loss of less than 0.1 wt %, based on the monomers in the feed stream.

COMPARATIVE EXAMPLE

A column having one plate was run on a feed stream of 20 t/h of monomeric styrene which had been stabilized with 15 ppm of 4-tert-butylcatechol (TBC). 450 t of the bottom mixture, containing 6000 ppm of 4-tert-butylcatechol (TBC), were recirculated by a circulating pump through an evaporator. The evaporator was operated at a temperature of 86° C. Within 3 days the polystyrene content of the bottoms in the evaporator, determined by measuring the solids content, rose to more than 25 wt %.

EXAMPLE

Using the same conditions as in the comparative example 500 kg per hour of air were introduced on the suction side of the circulating pump. The polystyrene content of the bottoms was at all times less than 1.2 wt %.

What is claimed is:

1. A process for the distillation of vinyl aromatic monomers in the presence of 4-tert-butylcatechol (TBC) and oxygen or an oxygen-containing gas wherein no aromatic nitro or amino compound is present in any effective amount to prevent polymerization.

2. A process as defined in claim 1, wherein the vinyl aromatic monomer used is styrene.

3. A process as defined in claim 1, wherein the 4-tert-butylcatechol is fed to a distillation assembly concurrently with the vinyl aromatic monomer, the concentration of 4-tert-butylcatechol in the bottom mixture of the distillation assembly being in a range of from 200 to 15,000 ppm based on the vinyl aromatic monomer.

4. A process as defined in claim 1, wherein the distillation is carried out under vacuum at temperatures ranging from 40° to 125°C.

5. A process as defined in claim 1, wherein the oxygen-containing gas is metered into the bottom mixture of a distillation assembly through a gas spray.

6. A process as defined in claim 1, wherein the oxygen-containing gas is metered in on the suction side of a circulating pump mounted upstream of a distillation assembly.

7. A process as defined in claim 1, wherein the oxygen is fed in at a rate of from 0.01 to 0.5 wt %, based on the weight of vinyl aromatic monomer.

* * * * *